United States Patent [19]

Mortensen

[11] 4,173,981

[45] Nov. 13, 1979

[54] CANNULA FOR ARTERIAL AND VENOUS BYPASS CANNULATION

[75] Inventor: J.D. Mortensen, Salt Lake City, Utah

[73] Assignee: University of Utah, Salt Lake City, Utah

[21] Appl. No.: 799,418

[22] Filed: May 23, 1977

[51] Int. Cl.² ............................................. A61M 25/00
[52] U.S. Cl. ...................................................... 128/348
[58] Field of Search ................................... 128/348–351, 128/214 R, 214.4, 2.05 R, DIG. 9, 2 M

[56] References Cited

U.S. PATENT DOCUMENTS

| 3,598,126 | 8/1971 | Hoeltzenbein | 128/348 |
| 3,828,767 | 8/1974 | Spiroff | 128/2.05 R |
| 3,863,641 | 2/1975 | Popa | 128/350 R |
| 3,938,501 | 2/1976 | Erikson | 128/348 X |
| 3,991,756 | 11/1976 | Synder | 128/214 R |
| 4,072,146 | 2/1978 | Howes | 128/2.05 D |

FOREIGN PATENT DOCUMENTS 705681  3/1965  Canada ..................................... 128/348

OTHER PUBLICATIONS

Bourassa—Angiology—vol. 22, No. 6, Jun. 71, pp. 320–331.

Primary Examiner—Dalton L. Truluck
Attorney, Agent, or Firm—Criddle, Thorpe & Western

[57] ABSTRACT

A cannula suitable for total bypass procedures in arterial and venous cannulation for extracorporeal perfusion of blood. The cannula has a tapered body of sufficient length for peripheral cannulation and openings through the cannula wall appropriately positioned to provide fluid transfer at various anatomical diversion sites within a patient's circulatory system in accordance with flow requirements necessary to maintain proper circulation is disclosed. The cannula structure can be adapted for bidirectional as well as unidirectional flow to maintain circulation in extremities otherwise ignored by single-directional flow cannulation. Reinforcing structure is disclosed for developing the required strength characteristics for the cannula wall, particularly for arterial applications.

17 Claims, 4 Drawing Figures

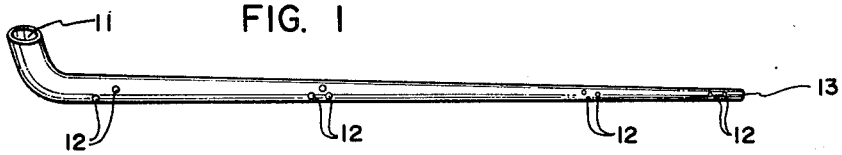
FIG. 1
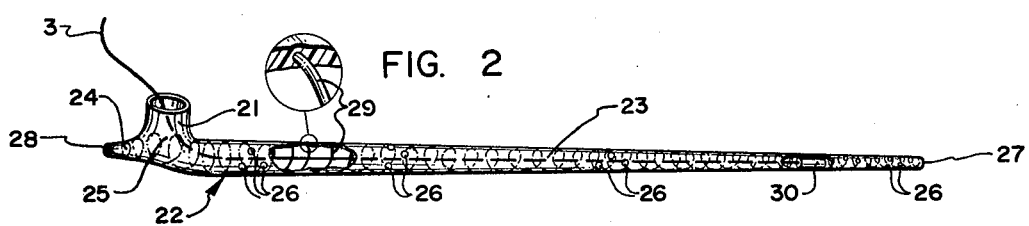
FIG. 2
FIG. 3
APPROXIMATE CANNULA LENGTH - 60.3cm
TAPER (I.D.) 9.5mm to 5.4mm at AORTIC TIP AND 1.5 ILIAC TIP
CANNULA WALL THICKNESS - 0.1mm
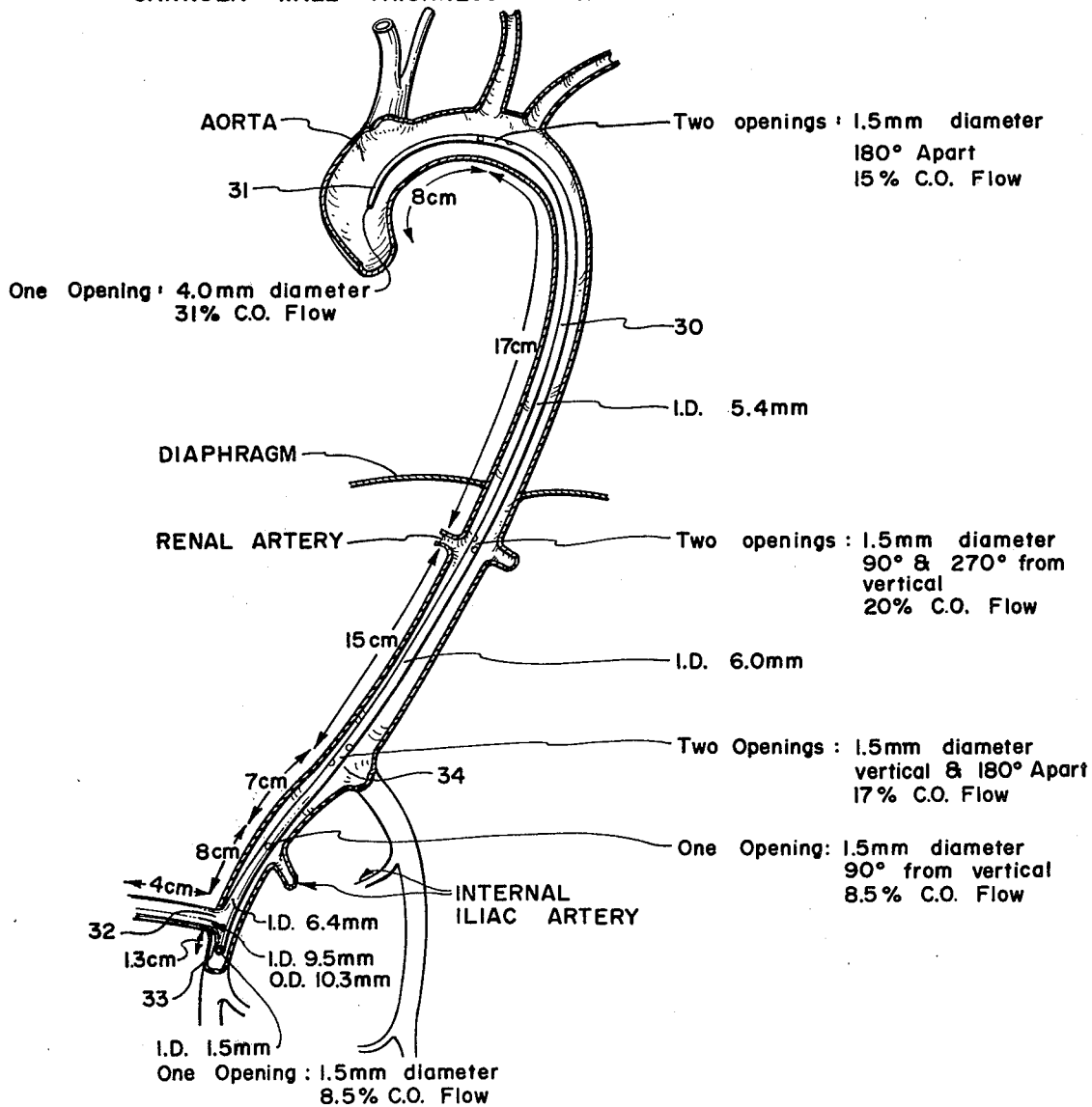

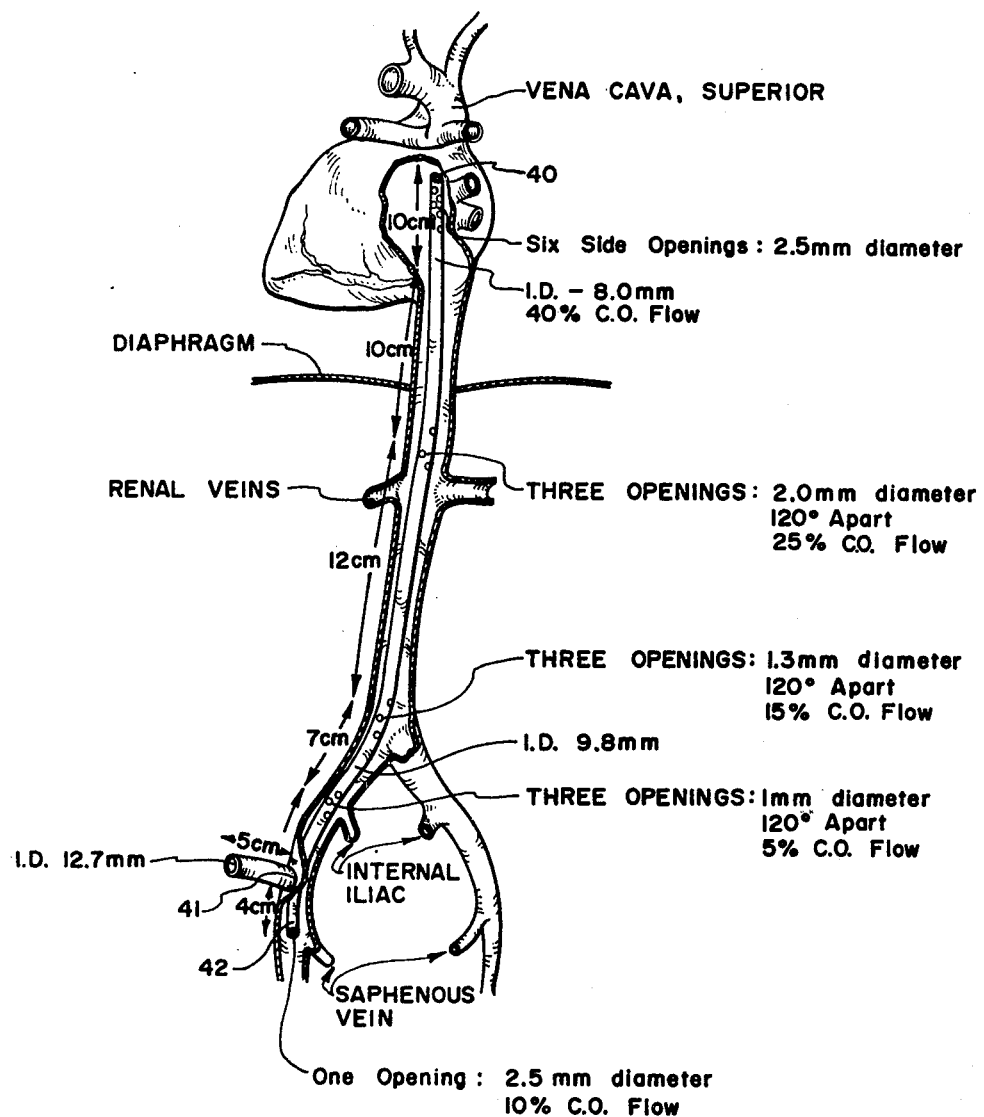

CANNULA FOR ARTERIAL AND VENOUS BYPASS CANNULATION

BACKGROUND OF THE INVENTION

This invention relates to cannulae for extracorporeal perfusion of fluid, and more particularly to peripheral cannulation procedures.

Numerous medical procedures involving the transfer of blood to or from a patient require cannulae to provide the fluid path. Such procedures include total and partial bypass of the heart and lungs, with the bypass route being a cannula appropriately seated within the circulatory system. In addition to bypass of a given section of the circulatory system (for example, the heart during open-heart surgery), extracorporeal transfer of the blood may have additional objectives such as artificial oxygenation of the blood as with a lung bypass procedure.

Conventional cannulae are effective in transporting fluid from an external source to the vein or artery affected; however, they are not designed to provide adequate dispersion by establishing flow gradients to maintain proper circulation through various tributaries of the subject vein or artery. They typically transport the blood to the artery or vein and allow natural fluid flow to seek the appropriate paths of distribution through the circulatory system. This procedure results in abnormal fluid pressures and inappropriate flow gradients at the point of extracorporeal entry as well as at branching locations of the subject vessel.

Furthermore, such cannulae typically possess thick wall structure, increasing the size of incision required to insert the cannula within the vessel. Where the cannulation procedure utilized required bidirectional flow to maintain blood in the extremities while infusing the major portion of blood toward the larger channels of circulation even larger or double incisions are required. Such larger incisions result from prior art techniques which require the use of separate cannulae inserted through a large single incision or two separate small incisions along the opposing bidirectional vessel paths, each cannula supplying fluid in accordance with the need of the particular portion of the circulatory system affected. Not only does this two cannula technique result in adverse flow characteristics at the respective points of entry, but the larger incision creates surgical difficulties such as increased risks of infection, seepage of blood, difficulty in post-operative repair and inordinate damage to tissue and vessels.

OBJECTS AND SUMMARY OF THE INVENTION

It is therefore an object of the present invention to provide an improved cannula suitable for arterial and venous cannulation procedures.

It is a further object of the present invention to provide a cannula capable of fluid transfer to various branching vessel networks to effect improved circulation during cannulation procedures.

It is an additional object of the present invention to provide a cannula having means for allocating fluid flow with respect to anatomical diversion sites to maintain proper circulation in a patient.

A still further object of the present invention is to provide a bidirectional flow cannula having a single access port which eliminates large or multiple incision requirements of conventional bidirectional cannulation.

It is yet another object of the present invention to provide a cannula for extracorporeal perfusion of fluids in general at higher flow rates and lower pressure gradients than formerly possible.

The above objects are realized in the present invention which comprises a cannula for the extracorporeal transfer of fluids to anatomical diversion sites within the circulatory system for maintaining flow gradients at such diversion sites in accordance with normal circulation. This invention is accomplished by utilizing a tubular member having a tapered body and inner and outer surfaces of blood and tissue compatible material. Openings are positioned along the length of the tubular member to correspond with anatomical diversion sites along the length of vessel to be subject to the cannulation procedure. The number, placement and size of such openings are determined by conventional methods to supply fluid therethrough in accordance with flow gradients necessary at the various diversion sites to maintain proper circulation. The tapered body of the cannula facilitates emplacement within the subject vessel and assists in the allocation of fluid flow through the various openings.

Bidirectional flow is obtained by having a single access port for transporting fluid through the extracorporeal path, said port joining a long tubular member near an end thereof to facilitate the emplacement of the tubular member within the vessel. Appropriate openings are provided along the length and at each end of the long tubular member to facilitate the desired rate of fluid transfer to the appropriate anatomical diversion sites.

The subject cannula represents a substantial improvement in cannula design, particularly in applications involving venous and arterial bypass procedures. Whereas prior art methods were limited in duration of cannulation, utilization of the subject cannula can be extended over long periods of time without adverse physiological effects. Furthermore, the subject cannula is well suited for pulsatile flow pumping which heretofore has not been practical with conventional cannulae. These benefits, as well as others apparent to those skilled in the art, will be more readily appreciated in view of the following detailed description.

DESCRIPTION OF THE DRAWINGS

FIG. 1 is a side view of a single-directional flow cannula in accordance with the present invention.

FIG. 2 shows a partially cutaway view of a bidirectional flow cannula having a wire reinforced tubular member.

FIG. 3 illustrates the positioning of a cannula of the present invention for total bypass, peripheral cannulation through an entry point on the external iliac artery.

FIG. 4 illustrates total bypass, peripheral cannulation on the venous side of the circulatory system through the external iliac vein.

DETAILED DESCRIPTION OF THE INVENTION

The present invention comprises a cannula useful in medical procedures involving the extracorporeal transfer of blood into and out of a patient's circulatory system.. Such cannulation procedures include arterial and venous bypass procedures in which the heart, lungs and certain segments of the circulatory system may be circumvented by conducting the circulating blood through an extracorporeal path. With respect to cardiac bypass, such procedures may be either total or partial bypass, each of which may be accomplished by central or peripheral cannulation. Inasmuch as central cannulation involves the risks of major surgery of the chest cavity, peripheral cannulation appears to be most viable of the various methods of bypass.

The cannula disclosed herein, although useful for certain methods of central cannulation as will be obvious to one of ordinary skill in the art, is particularly suitable for peripheral cannulation wherein the bypass procedures are accomplished by providing an extracorporeal transfer site through veins or arteries accessible without major surgery. Such transfer site locations include the groin, neck or arm. The length of the cannula is primarily determined by the distance from the extracorporeal transfer site to the most remote point of blood transfer. A typical length for an average size patient is forty to sixty centimeters where the entry site is in the groin region through the iliac artery or vein.

The primary function of the cannula is to transfer blood to or from specific locations within the circulatory system, while at the same time maintaining the necessary flow gradients thereat to ensure adequate blood supply throughout the various parts of the branching circulatory system affected.

Fig. 1 illustrates one embodiment of structure which accomplishes the coordinated transfer of blood while at the same time maintaining the appropriate flow gradients as required. A tubular structure is utilized to conform to the tubular anatomy of the circulatory system. The tube structure is tapered from the large end 11 to the smaller end 13. The large end is the extracorporeal transfer site from the circulatory system and would be connected to the appropriate medical instrumentation for oxygenation of the blood or other appropriate treatment. It is herefore imperative that the wall structure of this portion be of a nonporous nature to ensure containment of the patient blood within a sterile environment.

The tubular structure of the cannula is tapered from the larger opening 11 to the distal end 13 which is inserted into the vein or artery to be the subject of cannulation. The lumen within the cannula is likewise tapered to provide maximum inner diameter while at the same time retaining sufficient wall thickness to provide the strength necessary to withstand the arterial or venous pressures, whichever are applicable.

Openings 12 are positioned along the length of the cannula to provide fluid transfer paths to and from particular points of concern within the circulatory system. Ordinarily, these points of concern will be branching structure of the circulatory system which carries the blood to or from the expanding network of veins and arteries. For simplicity, these locations of branching arterial or venous networks will be referred to herein as anatomical diversion sites.

These sites further represent blood flow requirements which must be satisfied during cannulation to avoid adverse physiological effects. For example, failure to supply sufficient blood to the branching network of arteries such as the renal artery, iliac artery, femoral artery, etc., will result in starvation of tissue along the branching network therefrom with the occurrent risk of necrosis. On the other hand, excessive flow may result in pressure damage or vessel rupture. It is therefore imperative that cannulation procedures provide methods for the accurate direction of blood to the appropriate anatomical diversion sites in accordance with flow gradients designed to approximate the natural flow of blood through the circulatory system.

The location of openings 12 must therefore be appropriately determined by evaulating the area of cannulation and applying the appropriate anatomical parameters to establish hole opening diameter, contour location, and number required to maintain a proper fluid flow. Such calculations are well within the current state of the art. In addition, the tapered lumen diameter must be coordinated with the number and size of cannula openings to ensure that a sufficient supply of blood is provided in accordance with the referenced calculations.

In addition to the controlled flow provided by the tapered structure, insertion techniques are also facilitated, the minimal diameter of the distal end 13 having favorable size and maneuverability which is required to guide the cannula along the artery or vein during emplacement.

In view of the high flow requirements within the cannula body, it is preferred that a minimal wall thickness be provided. Among the limiting factors controlling wall thickness are the additional requirements for structural resilience, tensile strength and flexibility. Resilience and flexibility are necessary in order to insert and maneuver the cannula within the vein or artery lumen. Tensile strength is particularly important in arterial cannulation, in view of the fluid pressures reaching as high as 200 mm Hg.

The cannula of FIG. 1 is a single-directional flow cannula which is inserted into the vein or artery of interest, preferably through a peripheral entry point such as the iliac region, until the openings 12 are appropriately aligned with the anatomical structure of the area of cannulation. Blood can then be withdrawn from the vein or artery and extracted through the extracorporeal opening 11 or alternatively, can be introduced through this opening 11 and dispersed through the various nonextracorporeal openings 12 to accomplish the appropriate fluid transfer. In addition to openings 12 along the side of the cannula, the distal end 13 of the cannula body can also have open access.

Numerous materials can be utilized in the fabrication of the cannula body, for example copolyureathanes and similar block-copolymers are known to be blood and tissue compatible and also have the physical properties required of strength and resilience. In particular, a thin walled cannula can be constructed of this material having a thickness of about less than one millimeter and can be reinforced with an inlaid coil of thin wire.

FIG. 2 represents a second embodiment of the present invention, having bidirectional flow capability. This bidirectional cannula has three basic structural components comprising a nonporous segment 21 for extracorporeal transfer of blood from the main body or second section 22 of the cannula which consists of a long segment 23 and a short segment 24, each having appropriately displaced openings 26 and 28 along the length thereof.

The nonporous section 21 is located near an end of the second section 22 of the cannula to simplify emplacement within the circulatory system. With this near terminal configuration, the long segment 23 of the second section can be inserted into the vein or artery of interest to the appropriate location, whereupon the small section 24 can then be slipped through the same incision. Once the cannula is emplaced, the vein or artery is closed around the nonporous section 21 and the cannula is ready for service.

The nonporous section 21 is connected to the second section 22 of the cannula, dividing this second section into two segments, a long segment 23 and a short segment 24. The junction 25 of the nonporous section 21 with the second section 22 is open to permit free flow of blood therefrom to effect the desired extracorporeal fluid transfer through the second section.

As with the single-directional flow cannula previously discussed, the bidirectional cannula has openings 26 along the full length of the second section whose position and size are coordinated to provide the desired fluid flow gradients at each anatomical diversion site. In view of the short length of the short segment 24 a single opening 28 is provided and will normally meet the flow requirements. Likewise, the distal end 27 of the long segment may be open-ended to increase fluid flow capability.

To reduce fluid turbulence arising from the cross flow of fluids through the openings and against the fluid flow through the lumen of the cannula, a slanted cut through the cannula wall is preferable. The angle of slant of the opening should be sufficient to direct inflowing fluid toward a more parallel flow direction consistent with the direction of fluid flow down the length of the cannula.

The bidirectional flow cannula is tapered along the length of the second section 22 with the larger diameter occurring near the junction 25 of the extracorporeal transfer section with the second section of the cannula and decreasing along both sections therefrom. The taper of the short section 24 is extreme because of the short length and limited flow gradient requirement. The long segment has a more gradual taper which is coordinated with the relative positioning of the nonextracorporeal openings 26 to obtain the desired flow gradients. The degree of taper must be coordinated with the intended flow requirements to supply the necessary fluid amounts through the openings and may be calculated by conventional methods.

It is apparent in FIG. 2 that most of the relative fluid transfer will occur near the distal end 27 of the long segment 23 in view of the numerous openings. Failure to provide sufficient taper along the length of this segment would frustrate fluid flow to these openings and would therefore fail to provide adequate blood supply to reach the intended level of flow gradient into the corresponding region of the circulatory system.

The bidirectional cannula shown in FIG. 2 illustrates the wire reinforcing 29 which can be imbedded within the cannula wall. Also illustrated is an occluding member 30 which is positioned near the distal end 27 of the long segment of the cannula to block fluid flow during emplacement procedures. The emplacement location of the occluding member may be varied along the length of the second section 22 of the cannula depending upon the highest concentration of fluid flow through the openings therethrough. By utilization of an inflatable type occluding member release can be effected by simple deflation and withdrawal by an attached lead 31. For complete blockage, a balloon-type body conforming to the internal length and tapered diameter of the cannula lumen can be inflated within the cannula and retained therein during emplacement to occlude all fluid flow therethrough.

The bidirectional cannula has the added ability to maintain sufficient blood flow to the extremities located along the direction of flow from the short segment opening 28. Bidirectional flow occurs from the junction 25 of the extracorporeal nonporous section 21 to the distal ends thereof. Single-directional fluid flow occurs through the nonporous section to or from the treating apparatus located outside the patient's body. Cannulation can thereby be utilized to either transfer blood from an external source to the circulatory system or extract blood therefrom while maintaining the desired circulation.

The inventive concept of supplying controlled amounts of blood or fluid to a plurality of anatomical diversion sites and maintaining proper flow gradients thereat has numerous applications. Two specific embodiments of such applications are provided in FIGS. 3 and 4. Since it appears that the surgical aspects of peripheral cannulation are much preferred over the more dangerous methods of central cannulation, the disclosed figures have been directed to such methods. The dimensions, opening locations, and relative positioning of the cannula within the subject vessel will naturally vary with the size of the patient subject to the treatment.

It is anticipated that various sizes of cannulae could be constructed in accordance with the requirements of differing anatomical sizes. A typical selection of cannulae might include five sizes ranging from a small child size to large adult size. A patient requiring cannulation would simply be supplied with that size which most closely corresponds to his personal anatomy.

FIG. 3 illustrates the relative positioning of a bidirectional flow cannula 30 within a portion of the arterial system commencing at an insertion point through the external iliac artery 32 in the region of the groin and proceeding to the aortic opening 31 at the end of the cannula. The various cannula lengths, diameter openings and flow rates, shown as % of Cardiac Output (C.O.), illustrate a medium size cannula appropriate for total bypass, peripheral cannulation with entry through the right external iliac artery.

The cannula openings or sets of openings illustrated in FIG. 3 are shown with separation distances therebetween (8 cm, 17 cm, 15 cm, 7 cm, etc.) approximately equal to the distances between corresponding anatomical diversion sites to which they are adapted to transfer fluid. These openings are shown grouped with a first set of openings positioned toward a distal end of the cannula for transferring fluid with a cardiac region of diversion sites along an arched trunk of the patient's aorta. Second openings are positioned at a central region of the cannula for transferring fluid with renal artery diversion sites and third openings are positioned proximate to a projected entry site for the cannula for fluid transfer with a contralateral iliac artery diversion site.

For emplacement, the distal end 31 of the long segment is introduced through an incision on the external iliac artery 32 and is guided through the iliac toward the aorta and finally to its final position as shown. The figure illustrates the relative location of the openings with respect to the anatomical diversion sites of interest.

It will be noted that the short segment 33 of the second section of the cannula directs flow to the distal femoral artery through the single opening located at the distal end thereof. The long segment has a first opening for fluid transfer to the right internal iliac artery and second openings to establish the appropriate fluid gradient at the iliac bifurcation 34 of the aorta to feed the left iliac artery channel and network. A third set of openings is located in proximity to the renal artery diversion site and additional openings are located in the vicinity of the innominate, common carotid and subclavian arteries prior to the distal opening at the aortic entry from the heart, the combination denominated herein as the cardiac region. The respective opening diameters, orientation and cannula inner diameters and length have been confirmed for utility in actual total bypass cannulation procedures.

As indicated, the arterial cannula of FIG. 3 is intended for medium size patients. Larger patients would naturally require cannulae having appropriately increased dimensions to meet the greater flow requirements at each diversion site. The inverse, of course, would be true with smaller patients and in both cases the relative variations could be accomplished with conventional methods of calculation.

Fluid flow within the cannula described in FIG. 3 will typically proceed from the external source through the nonporous section of the cannula and then diverge through the respective long and short segments of the second section. Flow requirements would be established by external equipment designed to pump fluid at requisite pressures.

Inasmuch as fluid pressures range from 0 to 200 millimeters on the arterial side of the circulatory system, the cannula must be capable of withstanding substantial pressure without rupture. To maintain such pressures at the desired diversion sites, a much higher pressure will be experienced within the cannula in view of the multiple dissipating openings along the length of the second section. It has been determined that to supply a 200 millimeter pressure at an opening from the referenced cannula of FIG. 3, pressures as high as 600 millimeters may be experienced within the cannula structure.

A second embodiment of the subject cannula is disclosed in FIG. 4, wherein total bypass, peripheral venous cannulation is accomplished through an entry site on the iliac vein. Here again, the cannula dimensions illustrated represent a medium sized cannula and appropriate modifications would be neccessary for larger or smaller patients. In the case of venous cannulation, the high pressures experienced on the arterial side are not present. Nevertheless, the negative pressure experienced on the venous side will cause collapse of the cannula structure unless the cannula has sufficient resilience to withstand such pressures.

Typically, these pressures may range from 0 to 80 millimeters of suction within the cannula to establish the necessary 0 to 15 millimeters experienced on the venous side of the circulatory system. As previously indicated, resilience can be improved by the use of wire reinforcing or similar structure within the cannula wall.

The cannula openings or sets of openings illustrated in FIG. 4 are shown with separation distances therebetween (10 cm, 10 cm, 12 cm, 7 cm, etc.) approximately equal to the distances between corresponding anatomical diversion sites to which they are adapted to transfer fluid. These openings are shown grouped with a first set of openings positioned toward a distal end of the cannula for transferring fluid with a cardiac region of diversion sites in the region of the vena cava. Second openings are positioned at a central region of the cannula for transferring fluid with renal vein diversion sites and third openings are positioned proximate to a projected entry site for the cannula for fluid transfer with a contralateral iliac vein diversion site.

The venous cannulation procedure illustrated in FIG. 4 would require insertion of the distal end 40 of the long segment through an incision 41 in the external iliac vein, with the long segment being guided along the iliac vein through the lower vena cava to the approximate location of the superior vena cava. The short segment 42 of the second section of the cannula is slipped into the lower opening of the external iliac vein as shown.

Insertion techniques for cannulation utilizing the present invention will typically require some form of stylet which serves to guide the long segment of the cannula toward its desired location. Usually a form of lubricant is desired over the exterior surface of the cannula to reduce muscle contraction in response to irritation caused by insertion.

In addition to the suggested uses of cardiac or lung bypass, it is envisioned that other potential applications for fluid transfer into the circulatory system could utilize the cannula of the present invention. Localized perfusion of chemotherapeutic agents, for example, may be accomplished by use of a cannula having specified openings at regions where release of the particular therapeutic agent is desired. Such techniques would more effectively limit concentrated contact of transferred fluid to areas of critical need, and thereby minimize the risk associated with the more dangerous chemotherapeutic agents.

We claim:

1. A cannula for partial emplacement within a patient's circulatory system to effect extracorporeal fluid transfer therewith, said cannula including a tubular member having inner and outer surfaces of blood and tissue compatible material, and further comprising a nonporous tube section for accomplishing extracorporeal fluid transfer to or from a second tube section which communicates therewith through a junction occurring at a terminal portion of said nonporous tube section with a nonterminal portion of said second tube section, said second tube section having concurrent bidirectional flow capability along bidirectional paths commencing at said junction and continuing toward distal ends of said second tube section, said second tube section having a tapered body along at least one of the bidirectional paths toward said distal ends, said second tube section having a plurality of openings located along the length thereof to effect proper fluid transfer.

2. A cannula as defined in claim 1, wherein said communicating junction is located near one of the distal ends of said second tube section, said junction dividing said section tube section into short and long segments respectively.

3. A cannula as defined in claim 1, wherein one or both of said distal ends are open to effect fluid flow therethrough, said openings being coordinated in location and size to establish a proper flow gradient therethrough in accordance with flow requirements of a projected anatomical diversion site to be communicating therewith.

4. A cannula as defined in claim 1, further comprising a releasable occluding member located within said tubular member for impeding fluid flow therethrough during emplacement of said cannula within the circulatory system, said occluding member being capable of release to provide an open flow path when emplacement is completed without adverse displacement of said cannula from a desired location.

5. A cannula as defined in claim 4, wherein said occluding member is an inflatable element which can be inflated within said cannula to substantially block fluid flow therein and can be subsequently deflated to a nonobstructing location.

6. A cannula as defined in claim 1, wherein said tubular member has sufficient tensile strength to withstand pressures associated with transfer of fluid to an arterial system environment, said opening sizes and locations being coordinated with anatomical diversion sites of a portion of the arterial system.

7. A cannula as defined in claim 1, wherein said openings traverse said tubular member at an angle having a vector component directionally parallel to a primary direction of flow for said fluid within said circulatory system.

8. A cannula as defined by claim 1, wherein said openings are positioned along said second tube section to provide means for fluid transfer in accordance with said following approximate percentages and sites:
  (a) 10% of fluid flow through said short segment whose tip is adapted to be directed toward a femoral diversion site,
  (b) 5% of fluid flow through said long segment from an internal iliac vein diversion site,
  (c) 15% of fluid flow through said long segment from a vicinity of the junction of the iliac vein with the vena cava inferior vein to obtain flow to internal iliac, femoral and saphenous veins branching from a second external iliac vein,
  (d) 25% of fluid flow through said long segment from a renal vein diversion site, and
  (e) 40% of fluid flow through said long segment from cardiac region diversion sites.

9. A cannula as defined in claim 1, wherein said openings being positioned and sized along said second tube section to to provide means for fluid transfer at indicated diversion sites in accordance with said following percentages and sites:
  (a) 8.5% of fluid flow through said short segment of a femoral artery diversion site,
  (b) 8.5% of fluid flow through said long segment to an internal iliac artery diversion site,
  (c) 17% of fluid flow through said long segment to a diversion site at a vicinity of a main branch to a contralateral iliac artery,
  (d) 20% of fluid flow through said long segment to a renal artery diversion site, and
  (e) 46% of fluid flow through said long segment to a cardiac region of diversion sites along the large trunk of the aorta.

10. A cannula as defined in claim 1, further comprising reinforcing material at said wall.

11. A cannula as defined in claim 10, wherein said reinforcing material comprises wire imbedded within a wall portion of the cannula.

12. A cannula adapted for partial emplacement in communication with arterial branches of a predetermined patient's circulatory system to effect extracorporeal fluid transfer therewith, comprising a tubular member having a tapered body and inner and outer surfaces of blood and tissue compatible material, said tubular member having a plurality of openings positioned along the length thereof, including first openings positioned toward a distal end of said cannula for transferring fluid with a cardiac region of diversion sites along an arched trunk of the patient's aorta, second openings positioned at a central region of the cannula for transferring fluid with renal artery diversion sites and third openings proximate to a projected entry site for said cannula for fluid transfer with a contralateral iliac artery diversion site, said respective first, second and third openings being separated along said cannula by distances approximately equal to corresponding distances between the respective aortic, renal and iliac diversion sites of the predetermined patient.

13. A cannula as defined in claim 12, further comprising additional openings proximate to the projected cannula entry site and spaced from said third openings at a distance at least as great as a separation distance between the iliac diversion site and an internal iliac artery diversion site of the projected patient to thereby develop fluid transfer for a femoral artery diversion site and branching diversion sites therefrom.

14. A cannula as defined in claim 12, wherein said tubular member includes a junction of nonporous tube section coupled at a terminal portion thereof to a nonterminal portion of the tubular member having said openings for fluid transfer to permit bidirectional flow from the junction along opposing lengths of said tubular member, said junction being positioned near said third openings.

15. A cannula adapted for partial emplacement in communication with venous branches of a predetermined patient's circulatory system to effect extracorporeal fluid transfer therewith, comprising a tubular member having a tapered body and inner and outer surfaces of blood and tissue compatible material, said tubular member having a plurality of openings positioned along the length thereof, including first openings positioned toward a distal end of said cannula for transferring fluid with a cardiac region of diversion sites, second openings positioned at a central region of the cannula for transferring fluid with renal vein diversion sites and third openings proximate to a projected entry site for said cannula for fluid transfer with a contralateral iliac vein diversion site, said respective first, second and third openings being separated along said cannula by distances approximately equal to corresponding distances approximately equal to corresponding distances between the respective cardiac, renal and iliac diversion sites of the predetermined patient.

16. A cannula as defined in claim 15, further comprising additional openings proximate to the projected cannula entry site and spaced from said third openings at a distance at least as great as a separation distance between the iliac diversion site and an internal iliac artery diversion site of the projected patient to thereby develop fluid transfer for a femoral vein diversion site and branching diversion sites therefrom.

17. A cannula as defined in claim 15, wherein said tubular member includes a junction of nonporous tube section coupled at a terminal portion thereof to a nonterminal portion of the tubular member having said openings for fluid transfer to permit bidirectional flow from the junction along opposing lengths of said tubular member with openings, said junction being positioned near said third openings.

* * * * *